(12) United States Patent
Li et al.

(10) Patent No.: US 12,073,583 B2
(45) Date of Patent: Aug. 27, 2024

(54) METHOD AND APPARATUS FOR LOCATING TUMOR AND RADIOTHERAPY SYSTEM

(71) Applicant: OUR UNITED CORPORATION, Xi'an (CN)

(72) Inventors: Jiuliang Li, Xi'an (CN); Zhongya Wang, Xi'an (CN); Hao Yan, Xi'an (CN); Chun Luo, Xi'an (CN)

(73) Assignee: Our United Corporation, Xi'an (CN)

( * ) Notice: Subject to any disclaimer, the term of this patent is extended or adjusted under 35 U.S.C. 154(b) by 293 days.

(21) Appl. No.: 17/628,187

(22) PCT Filed: Jul. 18, 2019

(86) PCT No.: PCT/CN2019/096523
§ 371 (c)(1),
(2) Date: Jan. 18, 2022

(87) PCT Pub. No.: WO2021/007849
PCT Pub. Date: Jan. 21, 2021

(65) Prior Publication Data
US 2022/0262030 A1    Aug. 18, 2022

(51) Int. Cl.
*G06T 7/70* (2017.01)
*A61N 5/10* (2006.01)
*G06T 7/30* (2017.01)

(52) U.S. Cl.
CPC .............. *G06T 7/70* (2017.01); *A61N 5/1077* (2013.01); *G06T 7/30* (2017.01); *G06T 2207/10116* (2013.01); *G06T 2207/30096* (2013.01)

(58) Field of Classification Search
CPC ........................ G06T 7/70; G06T 7/30; G06T 2207/10116; G06T 2207/30096; G06T 7/74; A61N 5/1077; A61N 2005/1061; A61N 5/1049

(Continued)

(56) References Cited

U.S. PATENT DOCUMENTS 11,132,798 B2    9/2021  Yan et al.
2006/0036156 A1*  2/2006  Lachaine .................. G06T 7/74
                                                             600/411

(Continued)

FOREIGN PATENT DOCUMENTS

CN        101843954 A    9/2010
CN        108273199 A    7/2018
(Continued)

OTHER PUBLICATIONS

China National Intellectual Property Administration, First office action of Chinese application No. 201980056202.9 issued on May 23, 2022, which is foreign counterpart application of this US application.

(Continued)

*Primary Examiner* — Michael Robert Cammarata
*Assistant Examiner* — Pardis Sohraby
(74) *Attorney, Agent, or Firm* — Knobbe, Martens, Olson & Bear, LLP

(57) ABSTRACT

Provided is a method for locating a tumor. The method includes: performing image registration on a projection image of the tumor and a first standard image to acquire a first offset; generating a second standard image based on the first offset; performing image registration on the projection image and the second standard image to acquire a second offset; and updating the second standard image based on the second offset and executing the operation of image registration on the projection image and the second standard image again in response to the second offset satisfying a virtual re-sampling condition; or outputting an accumulated offset in response to the second offset not satisfying the virtual re-sampling condition, wherein the accumulated offset is a sum of the first offset and the second offset acquired by executing the operation of image registration.

16 Claims, 8 Drawing Sheets

(58) Field of Classification Search
USPC .......................................................... 382/128
See application file for complete search history.

(56) References Cited

U.S. PATENT DOCUMENTS

| | | |
|---|---|---|
| 2006/0203958 A1 | 9/2006 | Nagamine et al. |
| 2010/0246915 A1* | 9/2010 | Yamakoshi .......... A61N 5/1049 378/4 |
| 2011/0194745 A1* | 8/2011 | Dafni .................... A61B 6/481 382/131 |
| 2017/0301100 A1* | 10/2017 | Karino ................. G06V 10/762 |
| 2020/0346036 A1* | 11/2020 | Li ......................... A61N 5/1039 |
| 2020/0368555 A1 | 11/2020 | Gou et al. |
| 2021/0016110 A1 | 1/2021 | Gou et al. |

FOREIGN PATENT DOCUMENTS

| | | |
|---|---|---|
| CN | 108635681 A | 10/2018 |
| CN | 109663221 A | 4/2019 |
| EP | 1759733 A2 | 3/2007 |
| JP | 2009189461 A | 8/2009 |
| JP | 2009201556 A | 9/2009 |
| JP | 2016150082 A | 8/2016 |
| WO | 2019019188 A1 | 1/2019 |

OTHER PUBLICATIONS

International search report of PCT application No. PCT/CN2019/096523 issued on Apr. 26, 2020.

* cited by examiner

METHOD AND APPARATUS FOR LOCATING TUMOR AND RADIOTHERAPY SYSTEM

CROSS-REFERENCE TO RELATED APPLICATION

This application is a U.S. national stage of PCT international patent application No. PCT/CN2019/096523 filed on Jul. 18, 2019, the disclosure of which is incorporated herein by reference in its entirety.

TECHNICAL FIELD

The present disclosure relates to the field of radiotherapy technologies, and in particular, relates to a method and an apparatus for locating a tumor, and a radiotherapy system.

BACKGROUND

Radiotherapy is an effective means of using radiotherapy equipment to treat a tumor. However, if the tumor is not accurately located, the tumor may not be effectively treated, and other normal organs may be even erroneously irradiated by rays emitted from the radiotherapy equipment to cause an injury. Therefore, it is very important to accurately locate the tumor in radiotherapy.

SUMMARY

Embodiments of the preset disclosure provide a method and an apparatus for locating a tumor and a radiotherapy system. The technical solution is as follows.

In one aspect, a method for locating a tumor is provided. The method includes: performing image registration on a projection image of the tumor and a first standard image to acquire a first offset; generating a second standard image based on the first offset; performing image registration on the projection image and the second standard image to acquire a second offset; updating the second standard image based on the second offset and executing the operation of image registration on the projection image and the second standard image again in response to the second offset satisfying a virtual re-sampling condition; or outputting an accumulated offset in response to the second offset not satisfying the virtual re-sampling condition, where the accumulated offset is a sum of the first offset and the second offset acquired by executing the operation of image registration.

In another aspect, an apparatus for locating a tumor is provided. The apparatus includes: a registration module, configured to perform image registration on a projection image of the tumor and a first standard image to acquire a first offset, where the registration module is further configured to perform image registration on the projection image and the second standard image to acquire a second offset; a generation module, configured to generate a second standard image based on the first offset; an update module configured to update the second standard image based on the second offset and execute the operation of image registration on the projection image and the second standard image again in response to the second offset satisfying a virtual re-sampling condition; and an output module configured to output an accumulated offset in response to the second offset not satisfying the virtual re-sampling condition, wherein the accumulated offset is a sum of the first offset and the second offset acquired by executing the operation of image registration.

In yet another aspect, an apparatus for locating a tumor is provided. The apparatus for locating a tumor includes: a processor and a memory; wherein the memory is configured to store computer execution instructions, and when the apparatus for locating a tumor runs, the processor is configured to execute the computer execution instructions stored in the memory, so that the apparatus for locating a tumor is caused to perform the method for locating a tumor according to the above aspect.

In still a further aspect, a storage medium is provided. The storage medium stores instructions therein, wherein when the storage medium runs on a processing component, the processing component is caused to perform the method for locating a tumor according to the above aspect.

In one additional aspect, a radiotherapy system is provided. The radiotherapy system includes: radiotherapy equipment, a host computer, a patient support apparatus, and an image-guided system; wherein the image-guided system includes the apparatus for locating a tumor according to the above aspect.

It should be understood that the above general description and the following detailed description are only exemplary and explanatory, and are not intended to limit the present disclosure.

BRIEF DESCRIPTION OF THE DRAWINGS

For clearer descriptions of the technical solutions in the embodiments of the present disclosure, the following briefly introduces the accompanying drawings required for describing the embodiments. Apparently, the accompanying drawings in the following description show merely some embodiments of the present disclosure, and persons of ordinary skill in the art may still derive other drawings from these accompanying drawings without creative efforts.

In the related art, an X-ray projection image of the tumor may be collected, and the collected X-ray projection image and a digitally reconstructed radiograph (DRR) image of the tumor are subjected to image registration to acquire an offset. If the offset is not within an offset accuracy range of the radiotherapy equipment, a treatment couch may be moved based on the offset acquired by registration, the X-ray projection image is resampled after moving the treatment couch, and the operation of image registration is performed again. If the offset is within the offset accuracy range, the position of the tumor after a patient is initially placed may be directly determined as the position of the tumor before collecting the X-ray projection image.

However, the method for locating a tumor in the related art has poor flexibility and lower efficiency.

DETAILED DESCRIPTION

For clearer descriptions of the objectives, technical solutions, and advantages of the present disclosure, embodiments of the present disclosure are described in detail hereinafter in combination with the accompanying drawings.

Figure 1:
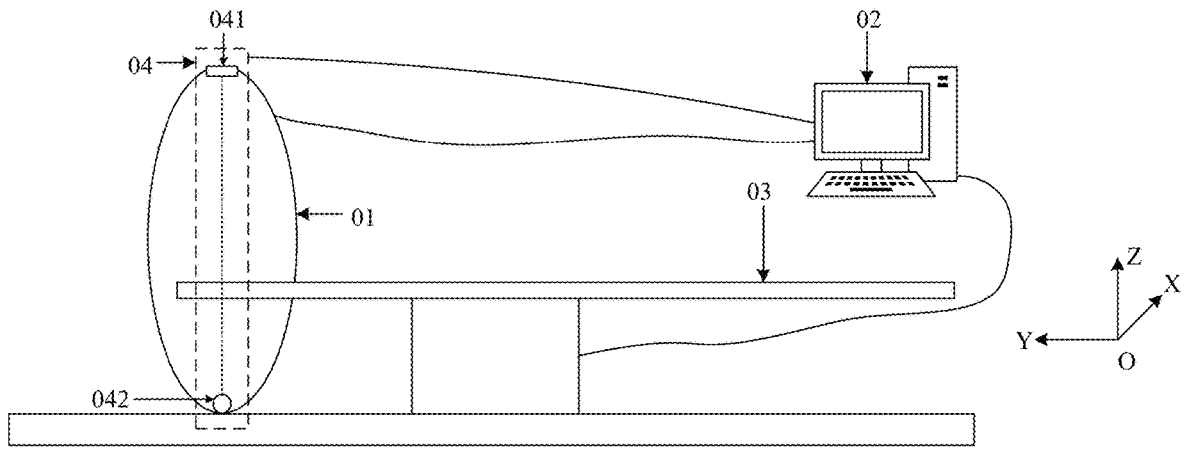
FIG. 1 is a schematic structural diagram of a radiotherapy system according to an embodiment of the present disclosure.

FIG. 1 is a schematic structural diagram of a radiotherapy system according to an embodiment of the present disclosure. As shown in FIG. 1, the radiotherapy system may include radiotherapy equipment 01, a host computer 02 (also be referred as a control system), a patient support apparatus 03, and an image-guided system 04. For example, referring to FIG. 1, the radiotherapy equipment 01 may include a radiotherapy gantry, and the patient support apparatus 03 may be a treatment couch. Optionally, the patient support apparatus 03 may also be other apparatuses for supporting the patient, for example, a treatment chair.

The host computer 02 may establish a communication connection with the radiotherapy gantry, the patient support apparatus 03 and the image-guided system 04. The host computer 02 may control the movement of the patient support apparatus 03 and the radiotherapy gantry, and may receive data transmitted by the image-guided system 04. For example, referring to FIG. 1, the communication connection manner may be wired connection. Of course, the communication connection manner may also be wireless connection.

The patient support apparatus 03 may send the supported patient into a treatment space formed by rotation of the radiotherapy gantry. The image-guided system 04 may include at least one group of image collection assembly, and the at least one group of image collection assembly may be disposed on the radiotherapy gantry. FIG. 1 only shows one group of image collection assembly disposed on the radiotherapy gantry. Each group of image collection assembly may include a detector 041 and a bulb tube 042 which are disposed oppositely. The bulb tube 042 may emit rays. The detector 041 may receive the rays emitted by the bulb tube 042. The image-guided system 04 may generate a projection image of the tumor based on the rays received by the detector 041.

Optionally, the bulb tube 042 may be a bulb tube capable of emitting kilovolt (KV)-level X-rays, and the detector 041 may be a flat-panel detector. Correspondingly, the projection image generated by the image-guided system 04 may be a KV-level X projection image.

During radiotherapy, in order to accurately locate the tumor and ensure treatment reliability of the tumor, the host computer 02 may control the rotation of the radiotherapy gantry, so that the bulb tube 042 disposed on the radiotherapy gantry emits the rays at different angles, and further the image-guided system 04 can collect the projection images of the tumor at different angles. Then, the image-guided system 04 can perform image registration on the collected projection images and a standard image of the tumor to acquire an offset of the tumor, and output the offset to the host computer 02, so that the host computer 02 reliably adjusts the position of the patient support apparatus 03 based on the received offset.

The standard image of the tumor may refer to a DRR image reconstructed and generated by the image-guided system 04 based on a pre-acquired computed tomography (CT) image of the tumor. The image registration may refer to that one image is designated as a standard image and another image is designated as an image to be registered. The purpose of registration is to enable that the coordinates of all points on the image to be registered coincide with the standard image.

Optionally, the standard image of the tumor may also be a magnetic resonance imaging (MRI) image, or may also be a positron emission tomography (PET) image, which is not limited in the embodiment of the present disclosure.

However, if there is a larger deviation between an actual position (that is, an initial placement position) and a theoretical position (that is, a beam focal point of treatment rays) of the tumor, for example, the deviation of a translation amount is about 10 to 15 mm, and the deviation of a rotation amount is about 3 degrees, then multiple times of image registration need to be performed to acquire a more accurate offset.

In the related art, the more accurate offset can be acquired by repeatedly moving the patient support apparatus, continuously collecting the projection images of the tumor, and performing image registration on the reacquired projection images and the standard image. However, it is time-consuming to repeatedly move the patient support apparatus and continuously collect the projection images, and the efficiency of radiotherapy is lower. In addition, prices of the patient support apparatus and the image collection assembly are relatively expensive. Therefore, due to repeated movement of the patient support apparatus and continuous use of the image collection assembly for collecting the projection images, the consumption of the patient support apparatus and the image collection assembly is relatively large, and the service life of the patient support apparatus the image capture assembly is shorter. In addition, since the current patient support apparatuses are all three-dimensional structures, the offsets in all directions cannot be reliably acquired, and the flexibility of radiotherapy is poor.

The embodiment of the present disclosure provides a method for locating a tumor, which can solve the problems of poor flexibility and low efficiency of the method for locating a tumor, and short service life of the patient support apparatus and the image collection assembly in the related art.

Figure 2:
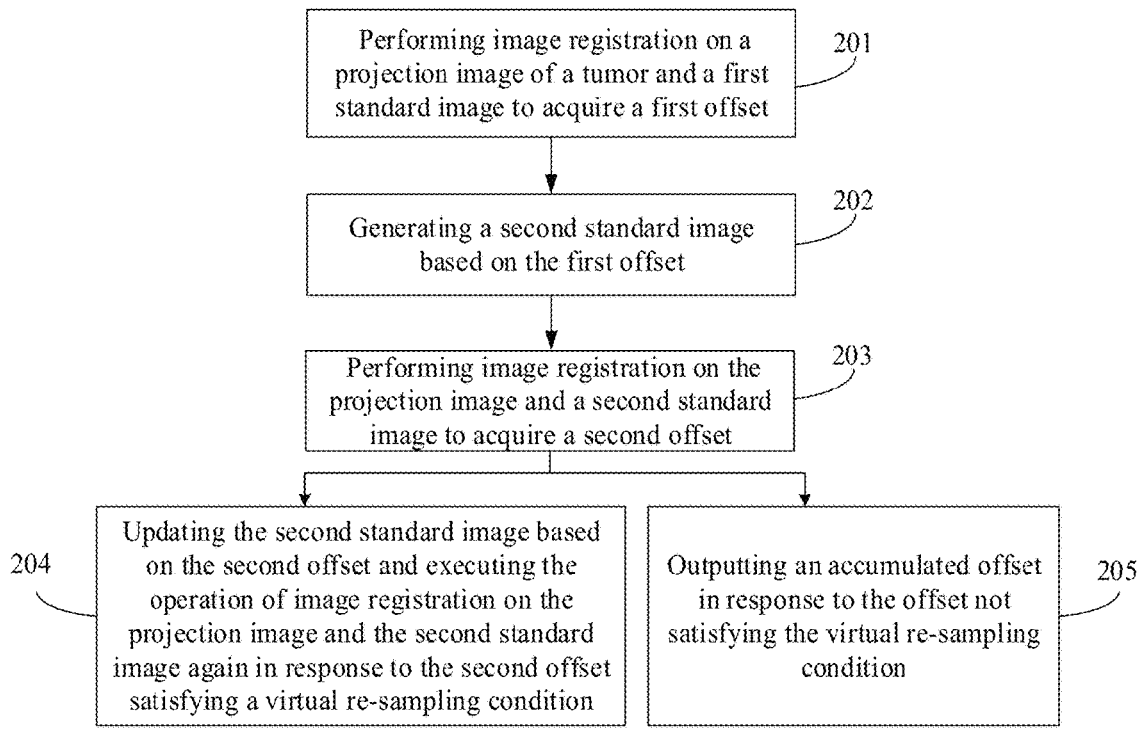
FIG. 2 is a flowchart of a method for locating a tumor according to an embodiment of the present disclosure.

FIG. 2 is a flowchart of a method for locating a tumor according to an embodiment of the present disclosure, which can be applied to an apparatus for locating a tumor. The apparatus for locating a tumor may be the image-guided system in the radiotherapy system shown in FIG. 1. As shown in FIG. 2, the method may include the following steps.

In step 201: image registration is performed on the projected image of the tumor and a first standard image to acquire a first offset.

Optionally, the projection image of the tumor may be an image (for example, the KV-level X-ray projection image) collected by the image-guided system through the image collection assembly. The first standard image may be a DRR image that is firstly reconstructed and generated by the image-guided system based on the pre-acquired CT image of the tumor for the first time. The projection image at each angle corresponds to one first standard image at the same angle. That is, for the projection image at each angle, the image-guided system can generate the DRR image at that angle based on the CT image of the tumor.

In the embodiment of the present disclosure, the projection image of the tumor may include: two projection images collected at two mutually orthogonal (that is, an angle interval is 90 degrees) or approximately orthogonal (that is, the angle interval is about 90 degrees) angles. Correspondingly, the first standard image may include: two DRR images reconstructed and generated at the two mutually orthogonal or approximately orthogonal angles. Therefore, during radiotherapy, the image-guided system can collect two projection images of the tumor at the two mutually orthogonal or approximately orthogonal angles respectively, and then generate two DRR images of the tumor at that two angles. Then, for the projection image at each angle, the image-guided system may use the projection image at that angle as the standard image, use the first standard image at that angle as the image to be registered, and perform image registration on the projection image and the first standard image at that angle. After the image registration on the projection images and the first standard images at that two angles is completed, the first offset can be acquired.

In step 202: a second standard image is generated based on the first offset.

In the embodiment of the present disclosure, the operation that the image-guided system generates the second standard image based on the offset acquired by image registration may also be referred to as a virtual re-sampling operation. Since the offset is generally larger after the patient is placed for the first time, in order to ensure the locating accuracy of the tumor under the premise of saving processing resources, after the first offset is acquired by image registration, the image-guided system may directly execute the virtual re-sampling operation. That is, in this case, the image-guided system may directly generate the second standard image based on the first offset, and continue to execute the operation of step 203 below.

In step 203: image registration is performed on the projection image and the second standard image to acquire a second offset.

After the image-guided system generates the second standard image, the projection image at each angle may be continuously used as the standard image. The second standard image at each angle may be used as new image to be registered. The image at the same angle can be used as the new image to be registered. The projection image and the second standard image at the same angle are subjected to image registration one by one to acquire the second offset.

In step 204: in response to the second offset satisfying a virtual re-sampling condition, the second standard image is updated based on the second offset, and the operation of image registration is performed on the projection image and the second standard image again.

In the embodiment of the present disclosure, the virtual re-sampling condition may include: the second offset is greater than an offset threshold. The offset threshold may be a fixed value pre-configured in the image-guided system.

Since the offset is proportional to a locating deviation of the tumor, in a case that the second offset is greater than the offset threshold, that is, when the second offset is still larger, it can be determined that the second offset satisfies the virtual re-sampling condition. In this case, the image-guided system may continue to perform the virtual re-sampling operation. That is, the image-guided system may update the most recently generated second standard image based on the second offset at this time, that is, continue to generate a new second standard image and perform the operation of the above step 203 again until the acquired second offset does not satisfy the virtual re-sampling condition, that is, until the second offset is less than or equal to the offset threshold. In a case that the second offset is less than or equal to the offset threshold, that is, when the second offset is smaller, it can be determined that the second offset does not satisfy the virtual re-sampling condition. In this case, the image-guided system may directly execute the operation of step 205 below without performing the virtual re-sampling operation.

In step 205: in a case that the offset does not satisfy the virtual re-sampling condition, an accumulated offset is output.

After the image-guided system executes the above step 203, and it is determined that the second offset does not satisfy the virtual re-sampling condition, that is, when it is determined that the second offset is less than or equal to the offset threshold, the image-guided system may output the accumulated offset to the host computer. Therefore, the host computer can realize accurate locating of the tumor based on the accumulated offset. The accumulated offset may be the sum of the first offset and the second offset acquired each time that the operation of image registration in step 203 is performed.

In summary, the embodiment of the present disclosure provides a method for locating a tumor. In the method, after image registration is performed between the projection image of the tumor with the first standard image to acquire the first offset, the second standard image is generated based on the first offset. When the second offset satisfies the virtual re-sampling condition, the second standard image can be updated based on the second offset, and the operation of image registration is performed again until the second offset does not satisfy the virtual re-sampling condition. Then the accumulated offset is output to realize accurate locating of the tumor. Since execution subjects for updating the second standard image and performing the operation of image registration are both the image-guided system, the method for locating a tumor provided by the embodiment of the present disclosure can realize accurate locating of the tumor without repeatedly moving the patient support apparatus and repeatedly collecting the projection images. The method for locating a tumor has higher flexibility and efficiency, and the method for locating a tumor can also prolong the service life of expensive devices such as the patient support apparatus and the image collection assembly.

Figure 3:
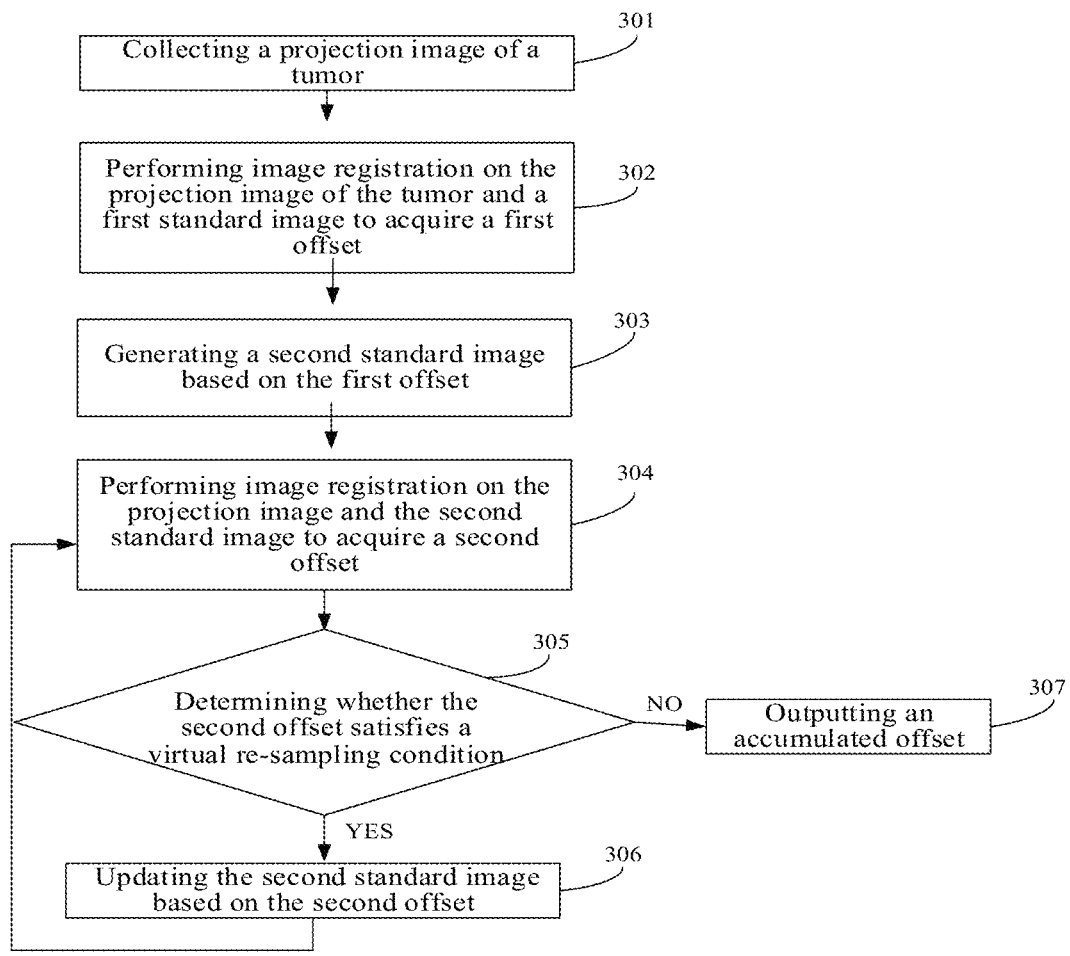
FIG. 3 is a flowchart of another method for locating a tumor according to an embodiment of the present disclosure.

In the following embodiment, the condition that the projection image is the KV-level X projection image, the standard image is the DRR image, and the patient support apparatus is the treatment couch is taken as an example for description. FIG. 3 is a flowchart of another method for locating a tumor provided by an embodiment of the present disclosure, which can be applied to an apparatus for locating a tumor. The apparatus for locating a tumor may be the image-guided system in the radiotherapy system shown in FIG. 1. As shown in FIG. 3, the method may include the following steps.

In step 301: the projection image of the tumor is collected.

In the embodiment of the present disclosure, the projection image of the tumor may be an image collected by the image-guided system through the image collection assembly. In order to realize image registration, the image-guided system may firstly collect the projection images of the tumor at two different angles which are mutually orthogonal or approximately orthogonal. Optionally, the projection image of the tumor may include: a first projection image of the tumor at a first angle, and a second projection image of the tumor at a second angle. The first angle and the second angle may be mutually orthogonal or approximately orthogonal gantry angles.

As an optional implementation, if the image-guided system only includes a group of image collection assembly, the host computer may control the bulb tube in the image collection assembly to firstly emit rays at the first angle by controlling the rotation of the treatment gantry. Correspondingly, the image-guided system may collect the first projection image of the tumor at the first angle. Then the host computer may control the bulb tube to emit rays at the second angle by controlling the rotation of the treatment gantry. Correspondingly, the image-guided system may collect the second projection image of the tumor at the second angle.

Exemplarily, assuming that the first angle is 0 degree, and the second angle is 90 degrees. When the direction of a beam central axis of the rays emitted by the bulb tube is parallel to a width direction of the treatment couch, the first angle is 0 degree. When the direction of the beam central axis of the rays emitted by the bulb tube is perpendicular to the width direction of the treatment couch, the second angle is 90 degrees. Therefore, the host computer firstly control the rotation of the treatment gantry, so that the direction of the beam central axis of the rays emitted by the bulb tube can be parallel to the width direction of the treatment couch. In this case, the image-guided system can collect the first projection image of the tumor at 0 degree. Then, through the control of the host computer, the treatment gantry continues to rotate, so that the central axis direction of the beam of the rays emitted by the bulb tube is perpendicular to the width direction of the treatment couch. In this case, the image-guided system can collect the second projection image of the tumor at 90 degrees.

As another optional implementation, if the image-guided system includes two groups of image collection assembly, the host computer may control the bulb tube in one group of image collection assembly to emit rays at the first angle, and control the bulb tube in the other group of image collection assembly to emit rays at the second angle. Correspondingly, the image-guided system may respectively collect the first projection image of the tumor at the first angle and the second projection image of the tumor at the second angle.

In step 302: the projection image of the tumor and the first standard image are subjected to image registration to acquire the first offset.

Optionally, the first standard image may be the DRR image reconstructed and generated by the image-guided system based on the pre-acquired CT image of the tumor for the first time. The projection image at each angle corresponds to one first standard image at the same angle, that is, for the projection image at each angle, the image-guided system may generate the DRR image at that angle based on the CT image of the tumor. For example, it is assumed that the projection image of the tumor collected by the image-guided system includes the first projection image of the tumor at the first angle, and the second projection image of the tumor at the second angle, then the image-guided system may generate one DRR image at the first angle, and generate the other DRR image at the second angle based on the CT image.

During radiotherapy, for the projection image at each angle, the image-guided system may use the projection image as the standard image, use the first standard image at that angle as the image to be registered, and perform image registration on the projection image with the first standard image at that angle. After the image registration on the projection images and the first standard images at the two angles is completed, the first offset may be acquired. Optionally, the first offset may include: a first translation and a first rotation.

Figure 4:
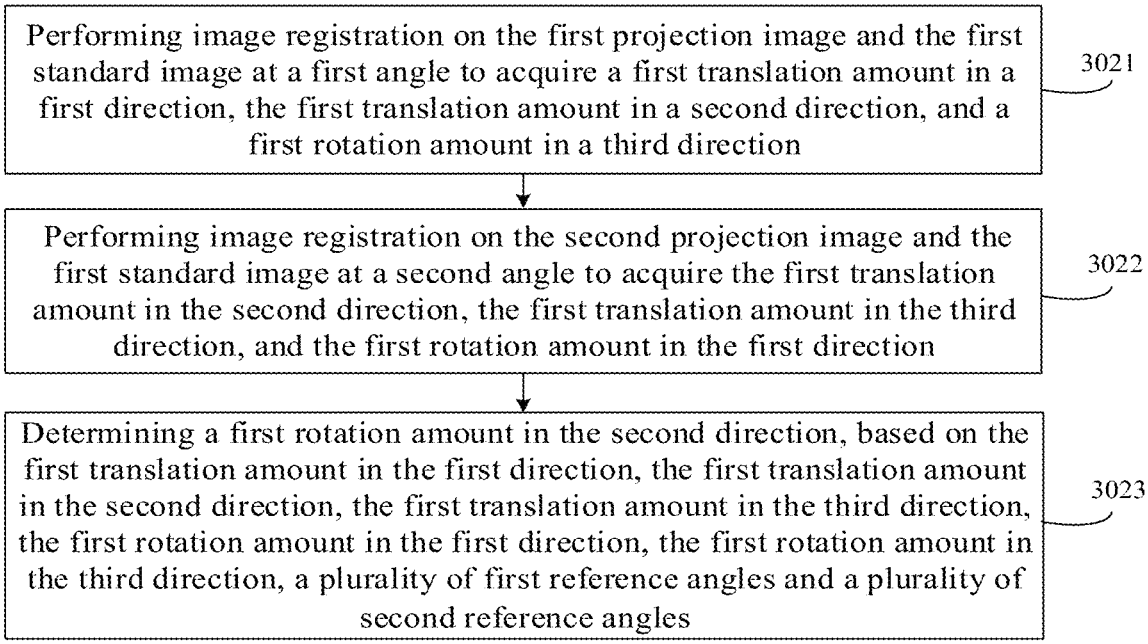
FIG. 4 is a flowchart of a method for acquiring a first offset according to an embodiment of the present disclosure.

The projection images of the tumor include: the first projection image of the tumor at the first angle, and the second projection image of the tumor at the second angle. The first angle being 0 degree and the second angle being 90 degrees are taken as an example below to introduce the process of performing image registration to acquire the first offset. FIG. 4 is a flowchart of a method for acquiring the first offset by performing image registration provided by an embodiment of the present disclosure. As shown in FIG. 4, the method may include the following steps.

In step 3021: image registration is performed on the first projected image and the first standard image at the first angle to acquire the first translation amount in a first direction, the first translation amount in a second direction, and the first rotation amount in a third direction.

In the embodiment of the present disclosure, the image-guided system may reconstruct and generate the first standard image of the first angle at the first angle based on the CT image of the tumor. Then, the image-guided system may perform image registration on the first standard image at the first angle and the first projection image to acquire the first translation amount in the first direction, the first translation amount in the second direction, and the first rotation amount in the third direction. Referring to FIG. 1, the first direction may be a height direction Z of the treatment couch 03, the second direction may be a length direction Y of the treatment couch 03, and the third direction may be a width direction X of the treatment couch 03. Each two of the first direction, the second direction and the third direction may be perpendicular to each other.

In step 3022: image registration is performed on the second projection image and the first standard image at the second angle to acquire the first translation amount in the second direction, the first translation amount in the third direction, and the first rotation amount in the first direction.

Similarly, the image-guided system may reconstruct and generate the first standard image of the second angle at the second angle based on the CT image of the tumor. Then, the image-guided system may perform image registration on the first standard image at the second angle and the second projection image to acquire the first translation amount in the second direction, the first translation amount in the third direction, and the first rotation amount in the first direction.

In step 3023: the first rotation amount in the second direction is determined based on the first translation amount in the first direction, the first translation amount in the second direction, the first translation amount in the third direction, the first rotation amount in the first direction, the first rotation amount in the third direction, a plurality of first reference angles, and a plurality of second reference angles.

The first reference angle may be an angle determined based on the first angle, and the second reference angle may be an angle determined based on the second angle. Optionally, an angle interval between every two adjacent first reference angles, and an angle interval between every two adjacent second reference angles may be both a first angle interval. The first angle interval may be an angle interval pre-configured in the image-guided system.

Optionally, the first reference angle may be an angle determined based on a continuously accumulated sum and a continuously accumulated difference of the first angle, the first angle interval, and a first preset angle adjustment range. The second reference angle may be an angle determined based on the continuously accumulated sum and the continuously accumulated difference of the second angle, the first angle interval, and the first preset angle adjustment range. The first preset angle adjustment range may be a pre-configured fixed range in the image-guided system, for example, the first preset angle adjustment range may be factory-configured in the image-guided system, or may be input into the image-guided system by a therapist.

Exemplarily, assuming that the first angle interval is 1 degree, and the first preset angle adjustment range is −3 degrees to 3 degrees. Based on the first angle of 0 degree, the first angle interval of 1 degree, and the first preset angle adjustment range of −3 degrees to 3 degrees, 7 first reference angles: −3 degrees, −2 degrees, −1 degree, 0 degree, 1 degree, 2 degrees and 3 degrees may be determined. Similarly, based on the second angle of 90 degrees, the first angle interval of 1 degree and the first preset angle adjustment range of −3 degrees to 3 degrees, 7 second reference angles: −87 degrees, −88 degrees, −89 degrees, 90 degrees, 91 degrees, 92 degrees and 93 degrees may be determined.

Figure 5:
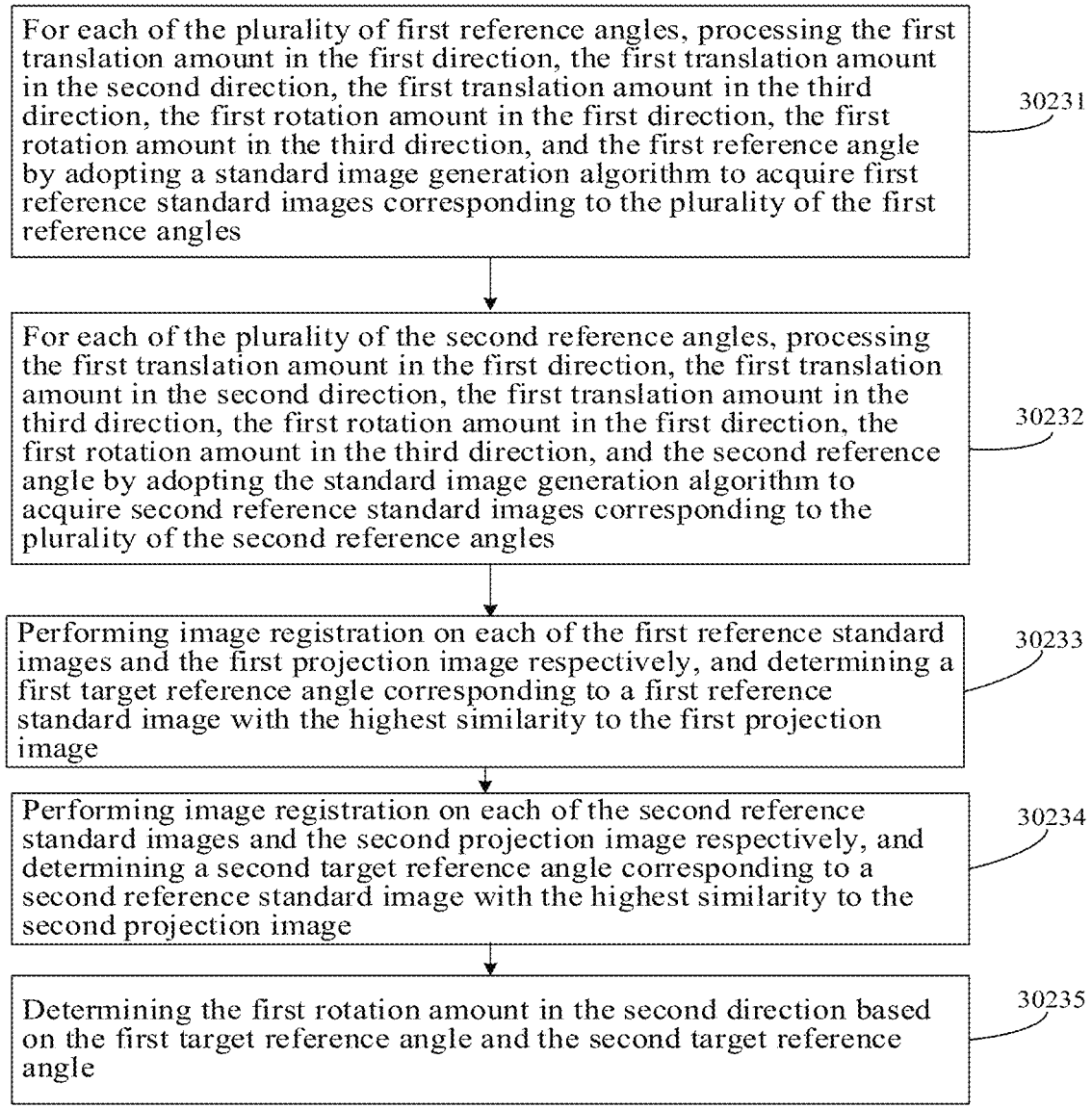
FIG. 5 is a flowchart of a method for determining a first rotation amount in a second direction according to an embodiment of the present disclosure.

FIG. 5 is a flowchart of a method for determining the first rotation amount in the second direction provided by an embodiment of the present disclosure. As shown in FIG. 5, the method may include the following steps.

In step 30231: for each of the plurality of first reference angles, a standard image generation algorithm is adopted to process the first translation amount in the first direction, the first translation amount in the second direction, the first translation amount in the third direction, the first rotation amount in the first direction, the first rotation amount in the third direction, and the first reference angle in order to acquire first reference standard images corresponding to the plurality of the first reference angles.

The standard image generation algorithm (that is, the DRR generation algorithm) may be an algorithm pre-configured in the image-guided system, for example, may be configured by a developer before the image-guided system leaves the factory.

In the embodiment of the present disclosure, for each first reference angle, the image-guided system may respectively substitute the acquired first translation amount in the first direction, the first translation amount in the second direction, the first translation amount in the third direction, the first rotation amount in the first direction, the first rotation amount in the third direction, and each first reference angle into the DRR generation algorithm, thereby generating the first reference standard image corresponding to the first reference angle.

Exemplarily, assuming that a total of 7 first reference angles: −3 degrees, −2 degrees, −1 degree, 0 degree, 1 degree, 2 degrees, and 3 degrees are acquired, the image-guided system may respectively substitute each of the 7 first reference angles and the remaining 5 parameters (that is, the first translation amount and the first rotation amount in the first direction, the first translation amount in the second direction, and the first translation amount and the first rotation amount in the third direction) into the DRR generation algorithm to acquire a first reference standard image group including 7 first reference standard images.

In step 30232: for each of the plurality of the second reference angles, the standard image generation algorithm is adopted to process the first translation amount in the first direction, the first translation amount in the second direction, the first translation amount in the third direction, the first rotation amount in the first direction, the first rotation amount in the third direction, and the second reference angle to acquire second reference standard images corresponding to the plurality of the second reference angles.

Similarly, for each second reference angle, the image-guided system may respectively substitute the first translation amount in the first direction, the first translation amount in the second direction, the first translation amount in the third direction, the first rotation amount in the first direction, the first rotation in the third direction, and each second reference angle into the DRR generation algorithm, thereby generating the first reference standard image corresponding to the second reference angle.

Exemplarily, assuming that 7 second reference angles: −87 degrees, −88 degrees, −89 degrees, 90 degrees, 91 degrees, 92 degrees, and 93 degrees are acquired, the image-guided system may respectively substitute each of the 7 second reference angles and the remaining 5 parameters into the DRR generation algorithm to acquire a second reference standard image group including 7 second reference standard images.

In step 30233: each of the first reference standard images is subjected to image registration with the first projection image respectively, and a first target reference angle corresponding to a first reference standard image which has the highest similarity to the first projection image is determined.

After the image-guided system acquires a plurality of first reference standard images, each first reference standard image in the first reference standard image group may be subjected to image registration with the first projection image respectively. One first reference standard image which has the highest similarity to the first projection image is determined as well as the first target reference angle corresponding to the first reference standard image which has the highest similarity.

Exemplarily, assuming that a total of 7 first reference standard images at the first reference angle are acquired, and the first reference angle corresponding to the first reference standard image which has the highest similarity to the first projection image in the 7 first reference standard images is 2 degrees, then it can be determined that the first target reference angle is 2 degrees.

In step 30234: each of the second reference standard images is subjected to image registration with the second projection image respectively, and a second target reference angle corresponding to a second reference standard image which has the highest similarity to the second projection image is determined.

Similarly, after the image-guided system acquires a plurality of second reference standard images, each of the second reference standard images in the second reference standard image group may be subjected to image registration with the second projection image respectively. One second reference standard image which has the highest similarity to the second projection image is determined as well as the second target reference angle corresponding to the second reference standard image which has the highest similarity.

Exemplarily, assuming that a total of 7 second reference standard images at the second reference angle are acquired, and the second reference angle corresponding to the second reference standard image which has the highest similarity to the second projection image in the 7 second reference standard images is 93 degrees, then it can be determined that the second target reference angle is 93 degrees.

In step 30235: the first rotation amount in the second direction is determined based on the first target reference angle and the second target reference angle.

As an optional implementation, the image-guided system may determine a difference between the first target reference angle and the first angle as the first rotation amount in the second direction. For example, assuming that the first target reference angle is 2 degrees, then the first rotation amount in the second direction may be: 2−0=2 degrees.

As another optional implementation, the image-guided system may determine a difference between the second target reference angle and the second angle as the first rotation amount in the second direction. For example, assuming that the second target reference angle is 93 degrees, then the first rotation amount in the second direction may be: 93−90=3 degrees.

As yet another optional implementation, the image-guided system may determine an average value of the difference between the first target reference angle and the first angle and the difference between the second target reference angle and the second angle as the first rotation amount in the second direction. Optionally, the average value may be a weighted average value, or may also be an arithmetic average value, which is not limited in the embodiment of the present disclosure.

Exemplarily, assuming that the average value is the arithmetic average value, the first target reference angle is 2 degrees, and the second target reference angle is 93 degrees, then the first rotation amount in the second direction may be: [(2−0)+(93−90)]/2==2.5 degrees.

In the above, the manner of determining the first rotation amount in the second direction by the average value of a difference between the first target reference angle and the first angle and a difference between the second target reference angle and the second angle can reduce the error of the method compared with the manner of directly determining the first rotation amount in the second direction as the difference between the first target reference angle and the first angle or the difference between the second target reference angle and the second angle.

In step 303: the second standard image is generated based on the first offset.

In the embodiment of the present disclosure, the operation that the image-guided system generates the second standard image based on the offset acquired by image registration may also be referred to as a virtual re-sampling operation. Since the offset is generally larger after the patient is placed for the first time, in order to ensure the locating accuracy of the tumor under the premise of saving processing resources, after the first offset is acquired by performing image registration, the image-guided system may directly execute the virtual re-sampling operation. That is, in this case, the image-guided system may directly generate the second standard image based on the first offset, and continue to execute the operation of step 304 below.

Optionally, the image-guided system may adopt the standard image generation algorithm to process the first translation amount in the first direction, the first translation amount in the second direction, the first translation amount in the third direction, the first rotation amount in the first direction, the first rotation amount in the second direction, and the first rotation amount in the third direction to acquire the second standard image. For example, the image-guided system may substitute the first translation amount in the first direction, the first translation amount in the second direction, the first translation amount in the third direction, the first rotation amount in the first direction, the first rotation amount in the second direction, and the first rotation amount in the third direction into the standard image generation algorithm to generate the second standard image.

In step 304: image registration is performed on the projection image and the second standard image to acquire a second offset.

In the embodiment of the present disclosure, after the image-guided system generates the second standard image, the image registration may be continuously performed on the projection image of the tumor and the corresponding second standard image to acquire the second offset. Optionally, the second offset may also include: a second translation amount and a second rotation.

Figure 6:
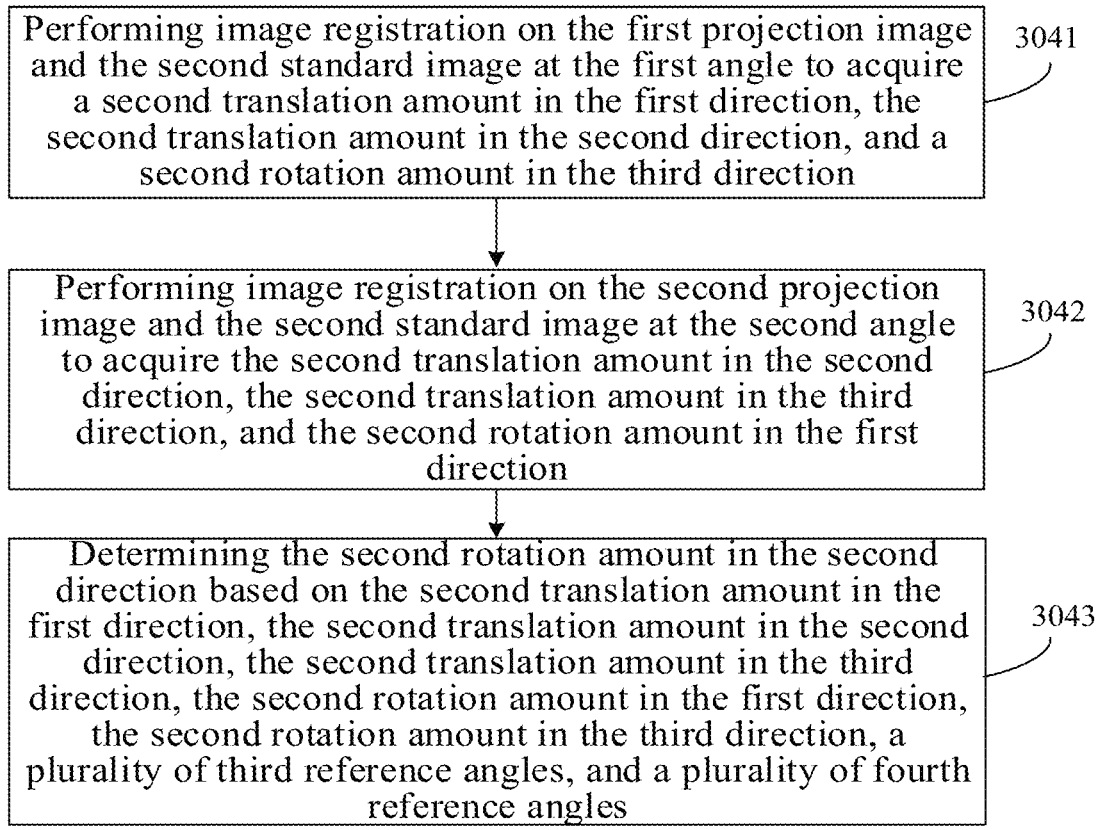
FIG. 6 is a flowchart of a method for acquiring a second offset according to an embodiment of the present disclosure.

The condition that the projection images of the tumor include: the first projection image of the tumor at the first angle, and the second projection image of the tumor at the second angle, the first angle is 0 degree and the second angle is 90 degrees is taken as an example below to introduce the process of performing image registration to acquire the second offset. FIG. 6 is a flowchart of a method for acquiring the second offset by performing image registration provided by an embodiment of the present disclosure. As shown in FIG. 6, the method may include the following steps.

In step 3041: image registration is performed on the first projection image and the second standard image at the first angle to acquire the second translation amount in the first direction, the second translation amount in the second direction, and the second rotation amount in the third direction.

The specific implementation of this step may refer to the above step 3021.

In step 3042: image registration is performed on the second projection image and the second standard image at the second angle to acquire the second translation amount in the second direction, the second translation amount in the third direction, and the second rotation amount in the first direction.

The specific implementation of this step may refer to the above step 3022.

In step 3043: based on the second translation amount in the first direction, the second translation amount in the second direction, the second translation amount in the third direction, the second rotation amount in the first direction, the second rotation amount in the third direction, a plurality of third reference angles, and a plurality of fourth reference angles, the second rotation amount in the second direction is determined.

The third reference angle may be an angle determined based on the first angle and the first rotation amount in the second direction, and the fourth reference angle may be an angle determined based on the second angle and the first rotation amount in the second direction. Optionally, an angle interval between every two adjacent third reference angles and an angle interval between every two adjacent fourth reference angles may be both a second angle interval. The second angle interval may be an angle interval pre-configured in the image-guided system, and the value of the second angle interval may be less than the first angle interval. By means of making the second angle interval less than the first angle interval, the locating efficiency and accuracy can be improved.

Optionally, the third reference angle may be an angle determined based on a continuously accumulated sum and a continuously accumulated difference of the first angle, the first rotation amount in the second direction, the second angle interval, and an adjustment range of a second preset angle. The second reference angle may be an angle determined based on the continuously accumulated sum and the continuously accumulated difference of the second angle, the first rotation amount in the second direction, the second angle interval, and the adjustment range of the second preset angle. The adjustment range of the second preset angle may also be a fixed range pre-configured in the image-guided system. Besides, the adjustment range of the second preset angle may be less than the adjustment range of the first preset angle. By means of making the adjustment range of the second preset angle less than the adjustment range of the first preset angle, the locating accuracy of the tumor can be further improved.

Exemplarily, assuming that the determined first rotation amount in the second direction is 2.5 degrees, the second angle interval is 0.2 degree, and the adjustment range of the second preset angle is from −0.8 degree to 0.8 degree. Then, based on the first angle of 0 degree, the first rotation amount in the second direction of 2.5 degrees, the second angle interval of 0.2 degree, and the adjustment range of second preset angle of −0.8 degree to 0.8 degree, 9 third reference angles: 1.7 degrees, 1.9 degrees, 2.1 degrees, 2.3 degrees, 2.5 degrees, 2.7 degrees, 2.9 degrees, 3.1 degrees and 3.3 degrees may be determined. Similarly, based on the first angle of 90 degrees, the first rotation amount in the second direction of 2.5 degrees, the second angle interval of 0.2 degree, and the adjustment range of the second preset angle of −0.8 degree to 0.8 degree, 9 fourth reference angles: 91.7 degrees, 91.9 degrees, 92.1 degrees, 92.3 degrees, 92.5 degrees, 92.7 degrees, 92.9 degrees, 93.1 degrees and 93.3 degrees may be determined.

Figure 7:
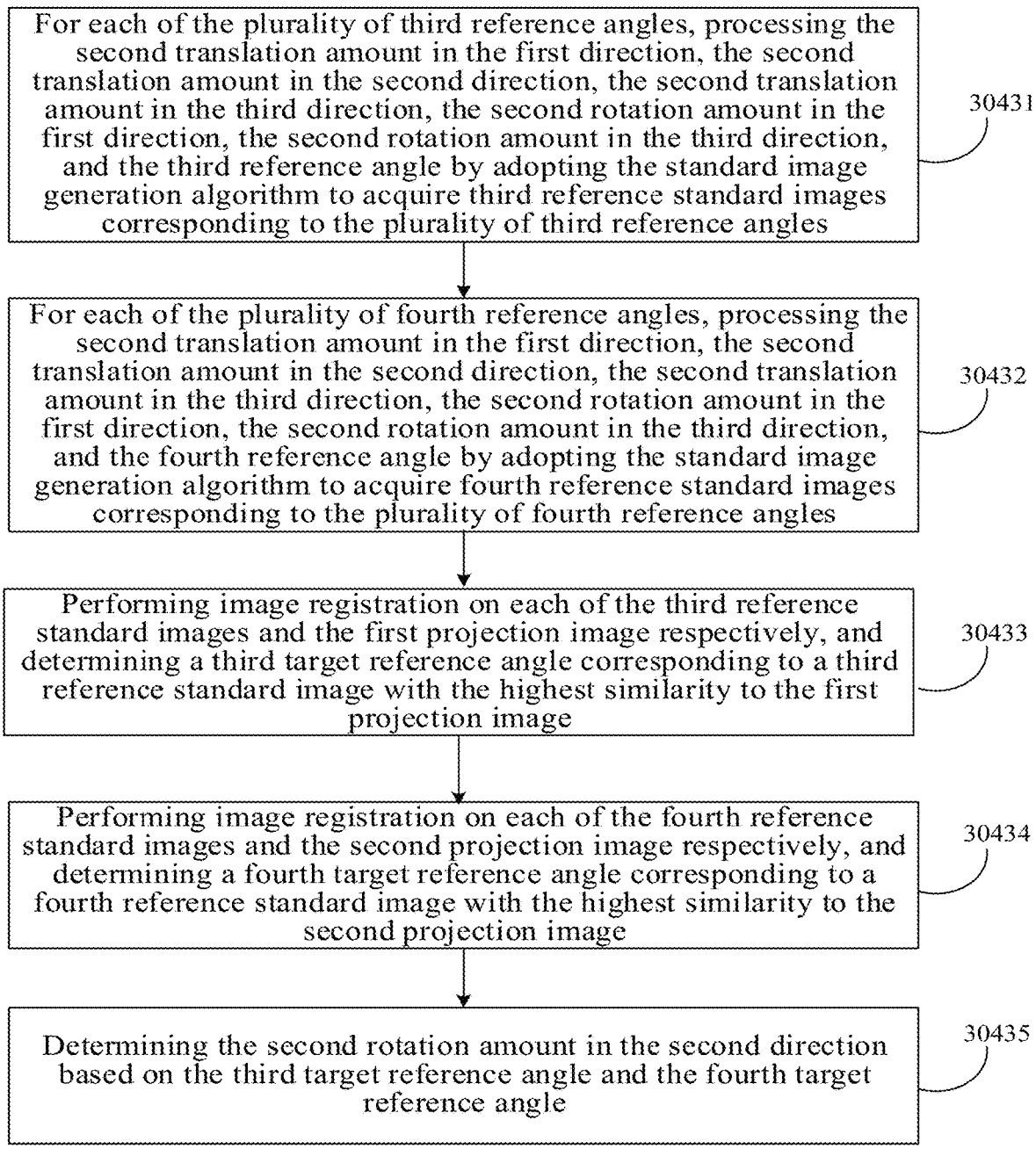
FIG. 7 is a flowchart of a method for determining a second rotation amount in the second direction according to an embodiment of the present disclosure.

FIG. 7 is a flowchart of a method for determining the second rotation in the second direction provided by an embodiment of the present disclosure. As shown in FIG. 7, the method may include the following steps.

In step 30431: for each of the plurality of third reference angles, the standard image generation algorithm is adopted to process the second translation amount in the first direction, the second translation amount in the second direction, the second translation amount in the third direction, the second rotation amount in the first direction, the second rotation amount in the third direction, and the third reference angle to acquire third reference standard images corresponding to the plurality of third reference angles.

The specific implementation of this step may refer to the above step 30231.

Exemplarily, assuming that a total of 9 third reference angles: 1.7 degrees, 1.9 degrees, 2.1 degrees, 2.3 degrees, 2.5 degrees, 2.7 degrees, 2.9 degrees, 3.1 degrees and 3.3 degrees are acquired, then the image-guided system may respectively substitute each of the 9 third reference angles and the remaining 5 parameters (that is, the second translation and the second rotation in the first direction, the second translation amount in the second direction, and the second translation and the second rotation in the third direction) into the standard image generation algorithm to acquire a third reference standard image group including 9 third reference standard images.

In step 30432: for each of the plurality of fourth reference angles, the standard image generation algorithm is adopted to process the second translation in the first direction, the second translation in the second direction, the second translation in the third direction, the second rotation in the first direction, the second rotation in the third direction, and the fourth reference angle to acquire fourth reference standard images corresponding to the plurality of fourth reference angles.

The specific implementation of this step may refer to the above step 30232.

Exemplarily, assuming that a total of 9 fourth reference angles: 91.7 degrees, 91.9 degrees, 92.1 degrees, 92.3 degrees, 92.5 degrees, 92.7 degrees, 92.9 degrees, 93.1 degrees and 93.3 degrees are acquired, then the image-guided system may respectively substitute each of the 9 fourth reference angles and the remaining 5 parameters into the standard image generation algorithm to acquire a fourth reference standard image group including 9 fourth reference standard images.

In step 30433: each of the third reference standard images is subjected to image registration with the first projection image respectively, and a third target reference angle corresponding to a third reference standard image which has the highest similarity to the first projection image is determined.

The specific implementation of this step may refer to the above step 30233.

Exemplarily, assuming that a total of 9 third reference standard images at the first angle are acquired, and the third reference angle corresponding to the third reference standard image with the highest similarity to the first projection image in the 9 third reference standard images at the first angle is 2.7 degrees, then it can be determined that the third target reference angle is 2.7 degrees.

In step 30434: each of the fourth reference standard images is subjected to image registration with the second projection image respectively, and a fourth target reference angle corresponding to a fourth reference standard image with the highest similarity to the second projection image is determined.

The specific implementation of this step may refer to the above step 30234.

Exemplarily, assuming that a total of 9 fourth reference standard images at the second angle are acquired, and the fourth reference angle corresponding to the fourth reference standard image with the highest similarity to the second projection image in the 9 fourth reference standard images at the second angle is 92.9 degrees, then it can be determined that the fourth target reference angle is 92.9 degrees.

In step 30435: the second rotation amount in the second direction is determined based on the third target reference angle and the fourth target reference angle.

As an optional implementation, the image guidance system may determine a difference between the third target reference angle and the first angle as the second rotation amount in the second direction. For example, assuming that the third target reference angle is 2.7 degrees, then the second rotation amount in the second direction may be: 2.7−0=2.7 degrees.

As another optional implementation, the image-guided system may determine a difference between the fourth target reference angle and the second angle as the second rotation amount in the second direction. For example, assuming that the fourth target reference angle is 92.9 degrees, then the second rotation amount in the second direction may be: 92.9−90=2.9 degrees.

As yet another optional implementation, the image-guided system may determine an average value of the difference between the third target reference angle and the first angle and the difference between the fourth target reference angle and the second angle as the second rotation amount in the second direction. Optionally, the average value may also be a weighted average value or an arithmetic average value.

Exemplarily, assuming that the average value is the arithmetic average value, the determined third target reference angle is 2.7 degrees, and the fourth target reference angle is 92.9 degrees, then the second rotation amount in the second direction is: [(2.7−0)+(92.9−90)]2=2.8 degrees.

In the above, the manner of determining the second rotation amount in the second direction by the average value of the difference between the third target reference angle and the first angle and the difference between the fourth target reference angle and the second angle can reduce the error of the method compared with the manner of directly determining the second rotation amount in the second direction as the difference between the third target reference angle and the first angle or the difference between the fourth target reference angle and the second angle.

It should be noted that in the embodiment of the present disclosure, a detection apparatus capable of measuring the rotation amount in the second direction may also be added in the second direction. The image-guided system may directly detect the first rotation amount in the second direction and the second rotation amount in the second direction through the detection apparatus. Optionally, the detection apparatus may be an infrared monitoring head marker, or may also be the image collection assembly.

In step 305: whether the second offset satisfies the virtual re-sampling condition is determined.

In the embodiment of the present disclosure, since the second offset includes: the second translation amount and the second rotation amount, the virtual re-sampling condition may include that the second translation amount is greater than a translation amount threshold, or the second rotation amount is greater than a rotation amount threshold. The translation amount threshold and the rotation amount threshold may be both a fixed value pre-configured in the image-guided system, for example, may be pre-configured when the image-guided system leaves the factory, or may be input to the image-guided system by the therapist during subsequent treatment. In addition, in order to ensure the locating accuracy of the tumor, the translation amount threshold and the rotation amount threshold may be both smaller. For example, the translation amount threshold may be 0.1 mm, and the rotation amount threshold may be 0.1 degree.

As an optional implementation, after the image-guided system acquires the second offset, whether the second translation amount in the second offset is greater than the translation amount threshold, and whether the second rotation amount in the second offset is greater than the rotation amount threshold may be firstly determined. If it is determined that the second translation amount is greater than the translation amount threshold, or the second rotation amount is greater than the rotation amount threshold, the image-guided system can automatically determine that the second offset satisfies the virtual re-sampling condition. In this case, the image-guided system can continue to perform step 306 below. If it is determined that the second translation amount is not greater than the translation amount threshold, and the second rotation amount is not greater than the rotation amount threshold, the image-guided system can automatically determine that the second offset does not satisfy the virtual re-sampling condition. In this case, the image-guided system can continue to perform step 307 below.

As another optional implementation, the image-guided system may also be provided with an indication switch corresponding to the "virtual re-sampling operation". Correspondingly, the image-guided system may directly determine that the second offset satisfies the virtual re-sampling condition when receiving an opening operation for the indication switch. For example, the therapist may trigger the "virtual re-sampling operation" to be turned on or off based on an image registration result and own experience.

In step 306: the second standard image is updated based on the second offset, and the operation of image registration is performed on the projection image and the second standard image again.

In the embodiment of the present disclosure, the image-guided system may perform the virtual re-sampling operation when determining that the second offset satisfies the virtual re-sampling condition. That is, in this case, the image-guided system may substitute the second translation amount in the first direction, the second translation amount in the second direction, the second translation amount in the third direction, the second rotation amount in the first direction, the second rotation amount in the second direction and the second rotation amount in the third direction into the standard image generation algorithm to regenerate the second standard image, and continue to perform the operation of image registration on the projection image and the updated (that is, the most recently generated) second standard image until it is determined that the second offset does not satisfy the virtual re-sampling condition after the above step 305 is performed.

In step 307: the accumulated offset is output.

The accumulated offset may be a sum of the first offset and each second offset acquired by executing the operation of image registration in the above step 305 every time. In the embodiment of the present disclosure, when determining that the second offset does not satisfy the virtual re-sampling condition, the image-guided system may directly output the accumulated offset to the host computer, so that the host computer can reliably move the position of the treatment couch based on the accumulated offset.

It should be noted that the first offset acquired after performing the above step 302 may also be less than or equal to the offset threshold. Therefore, in the present embodiment of the present disclosure, after the image-guided system acquires the first offset, whether the first offset satisfies the virtual re-sampling condition may be determined at first. If it is determined that the first offset satisfies the virtual re-sampling condition, then the operation of step 303 is continuously performed. If it is determined that the first offset does not satisfy the virtual re-sampling condition, the first offset is directly output to the host computer, so that the host computer can accurately locate the tumor based on the first offset. Since the first offset includes: the first translation amount and the first rotation amount, the virtual re-sampling condition may also include that the first translation amount is greater than the translation amount threshold, or the first rotation amount is greater than the rotation amount threshold. The two optional manners of determining whether the first offset satisfies the virtual re-sampling condition may refer to the two manners in the above step 306, which will not be repeated here.

Optionally, a coordinate system where the first offset is acquired by the image-guided system, or a coordinate system where the accumulated offset is acquired by the image-guided system may be different from a device coordinate system referred when the host computer adjusts the position of the treatment couch. Therefore, in order to ensure the locating reliability of the tumor, when acquiring the first offset or accumulated offset, the image-guided system may firstly convert each parameter in the first offset or the accumulated offset to the device coordinate system, and then output the converted offset to the host computer. Or, the acquired first offset or accumulated offset may also be output to the host computer, and the host computer realizes the coordinate conversion.

For example, assuming that the first offset or accumulated offset is located in the coordinate system of the treatment couch, the coordinate system of the treatment couch is a three-dimensional coordinate system composed of an axis X extending along the width direction of the treatment couch, an axis Y extending along the length direction of the treatment couch and an axis Z extending along the height direction of the treatment couch, and the device coordinate system referred to when the host computer adjusts the position of the treatment couch is a digital imaging and communications in medicine (DICOM) coordinate system. In this case, the image-guided system may firstly convert each parameter in the first offset or accumulated offset into the DICOM coordinate system after acquiring the first offset or accumulated offset, and then output the converted offset to the host computer.

Optionally, after acquiring the first offset or accumulated offset, the image-guided system may also display the acquired first offset or accumulated offset to the therapist for recording by the therapist.

It should also be noted that the sequence of the steps of the method for locating a tumor according to the embodiment of the present disclosure may be appropriately adjusted. For example, the above steps 301 and 302 may be performed simultaneously, and step 307 may be deleted as needed. Within the technical scope disclosed in the present disclosure, any variations of the method easily derived by those skilled in the art shall fall within the protection scope of the present disclosure, which is not repeated here.

In summary, the embodiment of the present disclosure provides a method for locating a tumor. In the method, after image registration is performed on the projection image of the tumor and the first standard image to acquire the first offset, the second standard image is generated based on the first offset. When the second offset satisfies the virtual re-sampling condition, the second standard image can be updated based on the second offset, and the operation of image registration is performed again until the second offset does not satisfy the virtual re-sampling condition. Then the accumulated offset is output to realize accurate locating of the tumor. Since execution subjects for updating the second standard image and performing the operation of image registration are both the image-guided system, the method for locating a tumor according to the embodiment of the present disclosure can realize accurate locating of the tumor without repeatedly moving the patient support apparatus and repeatedly collecting the projection images. The method for locating a tumor has higher flexibility and efficiency, and the method for locating a tumor can also prolong the service life of expensive devices such as the patient support apparatus and the image collection assembly.

Figure 8:
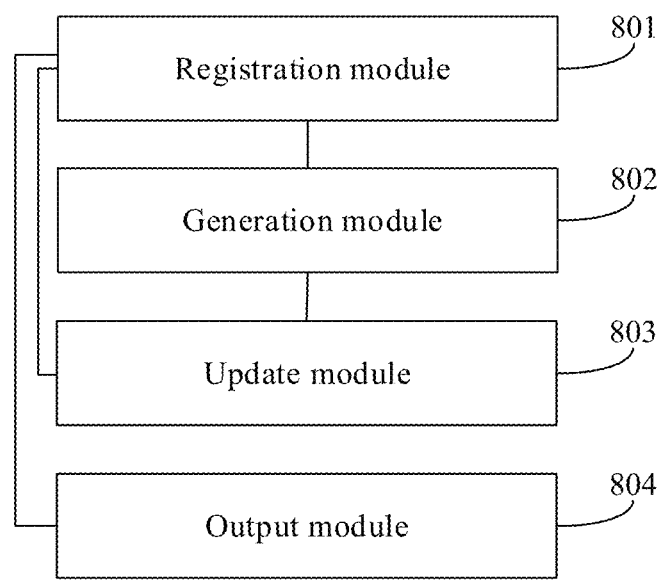
FIG. 8 is a schematic structural diagram of an apparatus for locating a tumor according to an embodiment of the present disclosure.

FIG. 8 is a schematic structural diagram of an apparatus for locating a tumor according to an embodiment of the present disclosure. As shown in FIG. 8, the apparatus may include:

a registration module 801 configured to perform image registration on a projection image of the tumor and a first standard image to acquire a first offset;

a generation module 802 configured to generate a second standard image based on the first offset;

optionally, the registration module 801 is further configured to perform image registration on the projection image and the second standard image to acquire a second offset;

an update module 803 configured to update the second standard image based on the second offset and execute the operation of image registration on the projection image and the second standard image again in response to the second offset satisfying a virtual re-sampling condition; and an output module 804 configured to output an accumulated offset in response to the second offset not satisfying the virtual re-sampling condition, where the accumulated offset is a sum of the first offset and the second offset acquired by executing the operation of image registration.

Optionally, the first offset may include: a first translation amount and a first rotation amount. The second offset may include: a second translation amount and a second rotation amount. Correspondingly, the virtual re-sampling condition may include that the second translation amount is greater than a translation amount threshold, or the second rotation amount is greater than a rotation amount threshold.

Figure 9:
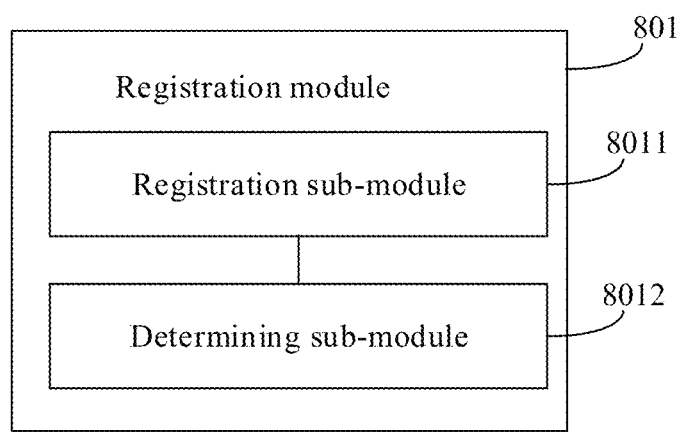
FIG. 9 is a schematic structural diagram of a registration module according to an embodiment of the present disclosure.

Optionally, the projection image may include: a first projection image of the tumor at a first angle, and a second projection image of the tumor at a second angle. FIG. 9 is a schematic structural diagram of the registration module according to an embodiment of the present disclosure. As shown in FIG. 9, the registration module 801 may include:

a registration sub-module 8011 configured to perform image registration on the first projection image and the first standard image at the first angle to acquire the first translation amount in a first direction, the first translation amount in a second direction and the first rotation amount in a third direction;

wherein the registration sub-module 8011 may also be configured to perform image registration on the second projection image and the first standard image at the second angle to acquire the first translation amount in the second direction, the first translation amount in the third direction, and the first rotation amount in the first direction; and a determining sub-module 8012 configured to, based on the first translation amount in the first direction, the first translation amount in the second direction, the first translation amount in the third direction, the first rotation amount in the first direction, the first rotation amount in the third direction, a plurality of first reference angles, and a plurality of second reference angles, determine the first rotation amount in the second direction.

The first reference angle is an angle determined based on the first angle, the second reference angle is an angle determined based on the second angle, and the first direction, the second direction and the third direction are perpendicular to each other.

Optionally, the determining sub-module 8012 may be configured to:

for each of the plurality of the first reference angles, process the first translation amount in the first direction, the first translation amount in the second direction, the first translation amount in the third direction, the first rotation amount in the first direction, the first rotation amount in the third direction, and the first reference angle by adopting a standard image generation algorithm to acquire first reference standard images corresponding to the plurality of the first reference angles;

for each of the plurality of the second reference angles, process the first translation amount in the first direction, the first translation amount in the second direction, the first translation amount in the third direction, the first rotation amount in the first direction, the first rotation amount in the third direction, and the second reference angle by adopting the standard image generation algorithm to acquire second reference standard images corresponding to the plurality of the second reference angles;

perform image registration on each first reference standard image and the first projection image respectively, and determine a first target reference angle corresponding to the first reference standard image with the highest similarity to the first projection image;

perform image registration on each of the second reference standard images and the second projection image respectively, and determine a second target reference angle corresponding to a second reference standard image with the highest similarity to the second projection image; and determine the first rotation amount in the second direction based on the first target reference angle and the second target reference angle.

Optionally, the determining sub-module 8012 may be configured to determine a difference between the first target reference angle and the first angle as the first rotation amount in the second direction; or, a difference between the second target reference angle and the second angle as the first rotation amount in the second direction; or, an average value of a difference between the first target reference angle and the first angle a the difference between the second target reference angle and the second angle as the first rotation amount in the second direction.

Optionally, the generation module 802 may be configured to: process the first translation amount in the first direction, the first translation amount in the second direction, the first translation amount in the third direction, the first rotation amount in the first direction, the first rotation amount in the second direction, and the first rotation amount in the third direction by adopting a standard image generation algorithm to acquire a second standard image. Correspondingly, referring to FIG. 9, the registration module 801 includes:

The registration sub-module 8011 may also be configured to perform image registration on the first projection image and the second standard image at the first angle to acquire the second translation amount in the first direction, the second translation amount in the second direction and the second rotation amount in the third direction.

The registration sub-module 8011 may also be configured to perform image registration on the second projection image and the second standard image at the second angle to acquire the second translation amount in the second direction, the second translation amount in the third direction and the second rotation amount in the first direction.

The determining sub-module 8012 may also be configured to determine the second rotation amount in the second direction based on the second translation amount in the first direction, the second translation amount in the second direction, the second translation amount in the third direction, the second rotation amount in the first direction, the second rotation amount in the third direction, a plurality of third reference angles, and a plurality of fourth reference angles.

The third reference angle is an angle determined based on the first angle and the first rotation amount in the second direction, and the fourth reference angle is an angle determined based on the second angle and the first rotation amount in the second direction.

Optionally, the determining sub-module 8012 may also be configured to:

for each of the plurality of third reference angles, process the second translation amount in the first direction, the second translation amount in the second direction, the second translation amount in the third direction, the second rotation amount in the first direction, the second rotation amount in the third direction, and the third reference angle by adopting the standard image generation algorithm to acquire third reference standard images corresponding to the plurality of third reference angles;

for each of the plurality of fourth reference angles, process the second translation amount in the first direction, the second translation amount in the second direction, the second translation amount in the third direction, the second rotation amount in the first direction, the second rotation amount in the third direction, and the fourth reference angle by adopting the standard image generation algorithm to acquire fourth reference standard images corresponding to the plurality of fourth reference angles;

perform image registration on each of the third reference standard images and the first projection image respectively, and determine a third target reference angle corresponding to a third reference standard image with the highest similarity to the first projection image;

perform image registration on each of the fourth reference standard images and the second projection image respectively, and determine a fourth target reference angle corresponding to a fourth reference standard image with the highest similarity to the second projection image; and determine the second rotation amount in the second direction based on the third target reference angle and the fourth target reference angle.

Optionally, the determining sub-module 8012 may be configured to determine a difference between the third target reference angle and the first angle as the second rotation amount in the second direction; or, determine a difference between the fourth target reference angle and the second angle as the second rotation amount in the second direction; or, determine an average value of a difference between the third target reference angle and the first angle and a difference between the fourth target reference angle and the second angle as the second rotation amount in the second direction.

Optionally, the angle interval between every two adjacent first reference angles and the angle interval between every two adjacent second reference angles are both a first angle interval.

The angle interval between every two adjacent third reference angles and the angle interval between every two adjacent fourth reference angles are both a second angle interval.

The second angle interval is less than the first angle interval.

Optionally, the first angle interval may be 1 degree, and the second angle interval may be 0.2 degree.

In summary, the embodiment of the present disclosure provides an apparatus for locating a tumor. According to the apparatus, after image registration is performed on the projection image of the tumor and the first standard image to acquire the first offset, the second standard image is generated based on the first offset. When the second offset satisfies the virtual re-sampling condition, the second standard image can be updated based on the second offset, and the operation of image registration is performed again until the second offset does not satisfy the virtual re-sampling condition. Then the accumulated offset is output to realize accurate locating of the tumor. Since execution subjects for updating the second standard image and performing the operation of image registration are both the image-guided system, the apparatus for locating a tumor according to the embodiment of the present disclosure can realize accurate locating of the tumor without repeatedly moving the patient support apparatus and repeatedly collecting the projection images. The apparatus for locating a tumor has higher flexibility and efficiency, and the apparatus for locating a tumor can also prolong the service life of expensive devices such as the patient support apparatus and the image collection assembly.

Regarding a placement apparatus in the foregoing embodiment, the specific manner in which each module executes the operation has been described in detail in the embodiment of the method, and the detailed description will not be repeated here.

Figure 10:
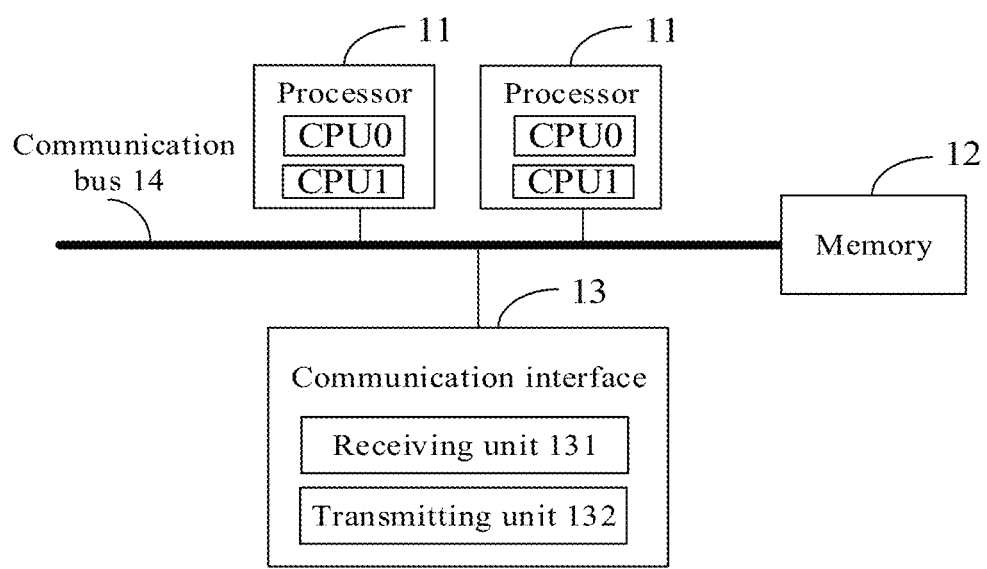
FIG. 10 is a schematic structural diagram of another apparatus for locating a tumor according to an embodiment of the present disclosure.

FIG. 10 is a schematic structural diagram of another apparatus for locating a tumor according to an embodiment of the present disclosure. As shown in FIG. 10, the apparatus for locating a tumor may include: a processor 11 and a memory 12. The memory 12 may be configured to store computer execution instructions. When the apparatus for locating a tumor runs, the processor 11 may be configured to execute the computer execution instructions stored in the memory 12, so that the apparatus for locating a tumor executes the method for locating a tumor as shown in any one of FIG. 2 to FIG. 7.

Optionally, referring to FIG. 10, the apparatus for locating a tumor may further include a communication interface 13 and a communication bus 14. The processor 11 may be a single processor, or may be a collective name of multiple processing elements. For example, the processor 11 may include at least one central processing unit (CPU); or may include an application specific integrated circuit (ASIC); or may include one or more integrated circuits configured to implement the embodiment of the present disclosure, for example a digital signal processor (DSP), or a field programmable gate array (FPGA). Each processor 11 may be a single-core processor (Single-CPU) or may be a multi-core processor (Multi-CPU). The processor 11 may refer to at least one of one or more devices, circuits, and processing cores for processing data (for example, the computer program instructions). For example, referring to FIG. 10, the apparatus for locating a tumor shown therein includes two processors 11 in total, and each processor 11 includes two CPUs: CPU0 and CPU1.

The memory 12 may be a read-only memory (ROM), a static storage device capable of storing static information and instructions, a random access memory (RAM), other types dynamic storage devices capable of storing the information and instructions, an electrically erasable programmable read-only memory (EEPROM), a compact disc read-only memory (CD-ROM), other compact disc storages and optical disc storages (including compression optical discs, laser discs, optical discs, digital universal optical discs and Blu-ray discs, etc.), a magnetic disk storage medium, other magnetic storage devices, or any other mediums that can carry or store desired program codes in the form of instructions or data structures and that can be accessed by a computer, but not limited to this. Optionally, the memory 12 may exist independently or the memory 12 may also be integrated with the processor 11. For example, referring to FIG. 10, the memory 12 shown therein exists independently, and the memory 12 may be connected to the processor 11 through the communication bus 14.

The communication interface 13 may be an apparatus such as a transceiver. The communication interface 13 may be configured to communicate with other devices or communication networks, such as a control system, a radio access network (RAN), or a wireless local area network (WLAN). The communication interface 13 may include a receiving unit 131 and realize a receiving function, and may include a transmitting unit 132 and realize a transmitting function. The communication bus 14 may be an industry standard architecture (ISA) bus, a peripheral component interconnect (PCI) bus, or an extended industry standard architecture (EISA) bus. The communication bus 14 may be an address bus, a data bus, or a control bus. Exemplarily, FIG. 10 only uses a thick line to represent the communication bus 14, but it does not mean that the communication bus 14 only includes one bus or one type of buses.

In addition, the embodiment of the present disclosure also provides a storage medium that stores instructions therein. When the storage medium runs on the processing component, the processing component is caused to execute the method for locating a tumor as shown in any one of FIG. 2 to FIG. 7.

The embodiment of the present disclosure also provides a radiotherapy system. As shown in FIG. 1, the radiotherapy system may include: radiotherapy equipment 01, a host computer 02, a patient support apparatus 03, and an image-guided system 04. The image-guided system 04 may include the apparatus for locating a tumor as shown in FIG. 10.

Those skilled in the art can clearly understand that, for convenience and concise description, the specific working process of the apparatuses and modules described above may refer to the corresponding process in the foregoing method embodiment, and will not be repeated here.

Described above are merely exemplary embodiments of the present disclosure, and are not intended to limit the present disclosure. Within the spirit and principles of the disclosure, any modifications, equivalent substitutions, improvements, and the like are within the protection scope of the present disclosure.

What is claimed is:

1. A method for locating a tumor, comprising:
performing image registration on a projection image of the tumor and a first standard image to acquire a first offset, wherein the projection image comprises: a first projection image of the tumor at a first angle and a second projection image of the tumor at a second angle, and the first offset comprises a first translation amount and a first rotation amount;
generating a second standard image based on the first offset;
performing image registration on the projection image and the second standard image to acquire a second offset; and
updating the second standard image based on the second offset and executing the operation of image registration on the projection image and the second standard image again in response to the second offset satisfying a virtual re-sampling condition; or
outputting an accumulated offset in response to the second offset not satisfying the virtual re-sampling condition, wherein the accumulated offset is a sum of the first offset and the second offset acquired by executing the operation of image registration;
wherein performing the image registration on the projection image of the tumor and the first standard image to acquire the first offset comprises:
performing image registration on the first projection image and a first standard image at the first angle to acquire a first translation amount in a first direction, a first translation amount in a second direction, and a first rotation amount in a third direction;

performing image registration on the second projection image and a first standard image at the second angle to acquire the first translation amount in the second direction, a first translation amount in the third direction, and a first rotation amount in the first direction; and determining a first rotation amount in the second direction based on the first translation amount in the first direction, the first translation amount in the second direction, the first translation amount in the third direction, the first rotation amount in the first direction, the first rotation amount in the third direction, a plurality of first reference angles, and a plurality of second reference angles;

wherein the first reference angle is an angle determined based on the first angle, the second reference angle is an angle determined based on the second angle, and the first direction, the second direction, and the third direction are perpendicular to each other.

2. The method according to claim 1, wherein the second offset comprises a second translation amount and a second rotation amount; and the virtual re-sampling condition comprises that the second translation amount is greater than a translation amount threshold or the second rotation amount is greater than a rotation amount threshold.

3. The method according to claim 1, wherein determining the first rotation amount in the second direction based on the first translation amount in the first direction, the first translation amount in the second direction, the first translation amount in the third direction, the first rotation amount in the first direction, the first rotation amount in the third direction, the plurality of first reference angles, and the plurality of second reference angles comprises:

for each of the plurality of the first reference angles, processing the first translation amount in the first direction, the first translation amount in the second direction, the first translation amount in the third direction, the first rotation amount in the first direction, the first rotation amount in the third direction and the first reference angle by adopting a standard image generation algorithm to acquire first reference standard images corresponding to the plurality of the first reference angles;

for each of the plurality of the second reference angles, processing the first translation amount in the first direction, the first translation amount in the second direction, the first translation amount in the third direction, the first rotation amount in the first direction, the first rotation amount in the third direction, and the second reference angle by adopting the standard image generation algorithm to acquire second reference standard images corresponding to the plurality of the second reference angles;

performing image registration on each of the first reference standard images and the first projection image respectively, and determining a first target reference angle corresponding to a first reference standard image with the highest similarity to the first projection image;

performing image registration on each of the second reference standard images and the second projection image respectively, and determining a second target reference angle corresponding to a second reference standard image with the highest similarity to the second projection image; and determining the first rotation amount in the second direction based on the first target reference angle and the second target reference angle.

4. The method according to claim 3, wherein determining the first rotation amount in the second direction based on the first target reference angle and the second target reference angle comprises:

determining a difference between the first target reference angle and the first angle as the first rotation amount in the second direction.

5. The method according to claim 3, wherein determining the first rotation amount in the second direction based on the first target reference angle and the second target reference angle comprises: determining a difference between the second target reference angle and the second angle as the first rotation amount in the second direction.

6. The method according to claim 3, wherein determining the first rotation amount in the second direction based on the first target reference angle and the second target reference angle comprises:

determining an average value of a difference between the first target reference angle and the first angle and a difference between the second target reference angle and the second angle as the first rotation amount in the second direction.

7. The method according to claim 2, wherein generating the second standard image based on the first offset comprises:

processing the first translation amount in the first direction, the first translation amount in the second direction, the first translation amount in the third direction, the first rotation amount in the first direction, the first rotation amount in the second direction and the first rotation amount in the third direction by adopting a standard image generation algorithm to acquire the second standard image; and performing image registration on the projection image and the second standard image to acquire the second offset comprises:

performing image registration on the first projection image and the second standard image at the first angle to acquire the second translation amount in the first direction, the second translation amount in the second direction, and the second rotation amount in the third direction;

performing image registration on the second projection image and the second standard image at the second angle to acquire the second translation amount in the second direction, the second translation amount in the third direction, and the second rotation amount in the first direction; and determining the second rotation amount in the second direction based on the second translation amount in the first direction, the second translation amount in the second direction, the second translation amount in the third direction, the second rotation amount in the first direction, the second rotation amount in the third direction, a plurality of third reference angles and a plurality of fourth reference angles;

wherein the third reference angle is an angle determined based on the first angle and the first rotation amount in the second direction, and the fourth reference angle is an angle determined based on the second angle and the first rotation amount in the second direction.

8. The method according to claim 7, wherein determining the second rotation amount in the second direction based on the second translation amount in the first direction, the second translation amount in the second direction, the second translation amount in the third direction, the second rotation amount in the first direction, the second rotation amount in the third direction, the plurality of third reference angles, and the plurality of fourth reference angles comprises:

for each of the plurality of third reference angles, processing the second translation amount in the first direction, the second translation amount in the second direction, the second translation amount in the third direction, the second rotation amount in the first direction, the second rotation amount in the third direction and the third reference angle by adopting the standard image generation algorithm to acquire third reference standard images corresponding to the plurality of third reference angles;

for each of the plurality of fourth reference angles, processing the second translation amount in the first direction, the second translation amount in the second direction, the second translation amount in the third direction, the second rotation amount in the first direction, the second rotation amount in the third direction, and the fourth reference angle by adopting the standard image generation algorithm to acquire fourth reference standard images corresponding to the plurality of fourth reference angles;

performing image registration on each of the third reference standard images and the first projection image respectively, and determining a third target reference angle corresponding to a third reference standard image with the highest similarity to the first projection image;

performing image registration on each of the fourth reference standard images and the second projection image respectively, and determining a fourth target reference angle corresponding to a fourth reference standard image with the highest similarity to the second projection image; and determining the second rotation amount in the second direction based on the third target reference angle and the fourth target reference angle.

9. The method according to claim 8, wherein determining the second rotation amount in the second direction based on the third target reference angle and the fourth target reference angle comprises:

determining a difference between the third target reference angle and the first angle as the second rotation amount in the second direction.

10. The method according to claim 8, wherein determining the second rotation amount in the second direction based on the third target reference angle and the fourth target reference angle comprises:

determining a difference between the fourth target reference angle and the second angle as the second rotation amount in the second direction.

11. The method according to claim 8, wherein determining the second rotation amount in the second direction based on the third target reference angle and the fourth target reference angle comprises:

determining an average value of a difference between the third target reference angle and the first angle and a difference between the fourth target reference angle and the second angle as the second rotation amount in the second direction.

12. The method according to claim 7, wherein, an angle interval between every two adjacent first reference angles, and an angle interval between every two adjacent second reference angles are both a first angle interval;

an angle interval between every two adjacent third reference angles, and an angle interval between every two adjacent fourth reference angles are both a second angle interval; and wherein the second angle interval is less than the first angle interval.

13. The method according to claim 12, wherein the first angle interval is 1 degree and the second angle interval is 0.2 degree.

14. An apparatus for locating a tumor, comprising a processor and a memory; and wherein the memory is configured to store computer execution instructions, and when the apparatus for locating a tumor runs, the processor is configured to execute the computer execution instructions stored in the memory, so that the apparatus for locating a tumor is caused to perform a method for locating a tumor, wherein the method comprises:

performing image registration on a projection image of the tumor and a first standard image to acquire a first offset, wherein the projection image comprises: a first projection image of the tumor at a first angle and a second projection image of the tumor at a second angle, and the first offset comprises a first translation amount and a first rotation amount;

generating a second standard image based on the first offset;

performing image registration on the projection image and the second standard image to acquire a second offset; and updating the second standard image based on the second offset and executing the operation of image registration on the projection image and the second standard image again in response to the second offset satisfying a virtual re-sampling condition; or outputting an accumulated offset in response to the second offset not satisfying the virtual re-sampling condition, wherein the accumulated offset is a sum of the first offset and the second offset acquired by executing the operation of image registration;

wherein performing the image registration on the projection image of the tumor and the first standard image to acquire the first offset comprises:

performing image registration on the first projection image and a first standard image at the first angle to acquire a first translation amount in a first direction, a first translation amount in a second direction, and a first rotation amount in a third direction;

performing image registration on the second projection image and a first standard image at the second angle to acquire the first translation amount in the second direction, a first translation amount in the third direction, and a first rotation amount in the first direction; and determining a first rotation amount in the second direction based on the first translation amount in the first direction, the first translation amount in the second direction, the first translation amount in the third direction, the first rotation amount in the first direction, the first rotation amount in the third direction, a plurality of first reference angles, and a plurality of second reference angles;

wherein the first reference angle is an angle determined based on the first angle, the second reference angle is an angle determined based on the second angle, and the first direction, the second direction, and the third direction are perpendicular to each other.

15. A radiotherapy system comprising: radiotherapy equipment, a host computer, a patient support apparatus, and an image-guided system;
wherein the image-guided system comprises the apparatus for locating a tumor according to claim 14.

16. A non-transitory storage medium storing instructions therein, wherein when the instructions run on a processing component, the processing component is caused to perform a method for locating a tumor, wherein the method comprises:
performing image registration on a projection image of the tumor and a first standard image to acquire a first offset, wherein the projection image comprises: a first projection image of the tumor at a first angle and a second projection image of the tumor at a second angle, and the first offset comprises a first translation amount and a first rotation amount;
generating a second standard image based on the first offset;
performing image registration on the projection image and the second standard image to acquire a second offset; and
updating the second standard image based on the second offset and executing the operation of image registration on the projection image and the second standard image again in response to the second offset satisfying a virtual re-sampling condition; or
outputting an accumulated offset in response to the second offset not satisfying the virtual re-sampling condition, wherein the accumulated offset is a sum of the first offset and the second offset acquired by executing the operation of image registration;
wherein performing the image registration on the projection image of the tumor and the first standard image to acquire the first offset comprises:
performing image registration on the first projection image and a first standard image at the first angle to acquire a first translation amount in a first direction, a first translation amount in a second direction, and a first rotation amount in a third direction;
performing image registration on the second projection image and a first standard image at the second angle to acquire the first translation amount in the second direction, a first translation amount in the third direction, and a first rotation amount in the first direction; and
determining a first rotation amount in the second direction based on the first translation amount in the first direction, the first translation amount in the second direction, the first translation amount in the third direction, the first rotation amount in the first direction, the first rotation amount in the third direction, a plurality of first reference angles, and a plurality of second reference angles;
wherein the first reference angle is an angle determined based on the first angle, the second reference angle is an angle determined based on the second angle, and the first direction, the second direction, and the third direction are perpendicular to each other.

* * * * *